United States Patent
Honda et al.

(12)

(10) Patent No.: US 6,255,463 B1
(45) Date of Patent: Jul. 3, 2001

(54) PRODUCTION OF AVERMECTIN COMPOUNDS

(75) Inventors: Masanori Honda; Hiroshi Kadoi; Hiromasa Morita; Isao Nagakura, all of Chita-gun (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/463,199

(22) PCT Filed: Jun. 25, 1998

(86) PCT No.: PCT/IB98/00988

§ 371 Date: Apr. 6, 2000

§ 102(e) Date: Apr. 6, 2000

(87) PCT Pub. No.: WO99/05156

PCT Pub. Date: Feb. 4, 1999

(51) Int. Cl.[7] .................................... C07M 1/00

(52) U.S. Cl. ............................. 536/7.1; 536/18.5

(58) Field of Search ..................... 536/7.1, 18.5

(56) References Cited

FOREIGN PATENT DOCUMENTS

| 0676236 | 3/1995 | (EP) . |
| 9522552 | 8/1995 | (WO) . |
| IB97/00916 | 7/1997 | (WO) . |

Primary Examiner—Elli Peselev
(74) Attorney, Agent, or Firm—Peter C. Richardson; Paul H. Ginsburg; Lorraine B. Ling

(57) ABSTRACT

This invention provides a process for preparing a compound of the formula (I):

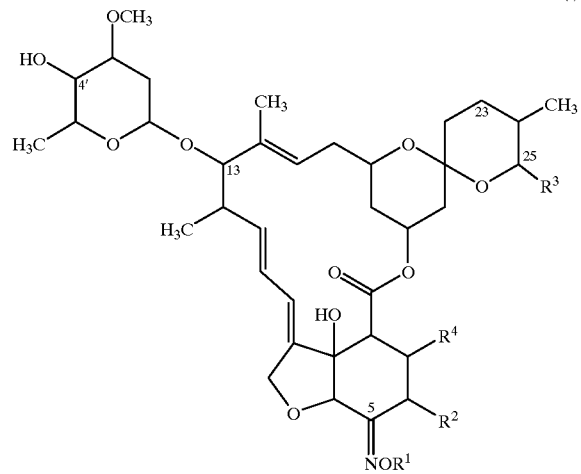

wherein $R^1$ is H or a hydroxyimino-protecting group; $R^2$ is H, $C_{1-4}$ alkyl or $C_{1-4}$ alkoxy; $R^3$ is $C_{1-8}$ alkyl, $C_{2-8}$ alkenyl or $C_{3-8}$ cycloalkyl, and $R^4$ is H, halo, $C_{1-4}$ alkyl or $C_{1-4}$ alkoxy, which process comprises the steps of (a) reacting an avermectin B2 derivative with an oxidizing agent to form a 5-oxo compound; (b) allowing the 5-oxo compound to react with a compound of formula $R^1$—O—$NH_2$ wherein $R^1$ is H or a hydroxyimino-protecting group, to form a 5-imino compound; (c) reacting the 5-imino compound with a thionocarbonizing agent to form a 4", 23-bisthionocarbonyl ester; (d) reacting the 4", 23-bisthionocarbonyl ester with a deoxygenation agent to form a 4", 23-dideoxy compound; and (e) reacting the R", 23-dideoxy compound with an acid to form a compound of the formula (I).

14 Claims, No Drawings

PRODUCTION OF AVERMECTIN COMPOUNDS

CROSS-REFERENCE TO RELATED APPLICATIONS

This application is the National Stage of International Application No. PCT/IB98/00988, filed Jun. 25, 1998, which claims the benefit of National Stage of International Application No. PCT/IB97/00916, filed Jul. 23, 1997.

TECHNICAL FIELD

This invention relates to a novel and improved process for preparing an avermectin compound of the formula (I) from an avermectin B2 compound of the formula (II), a fermentation derived avermectin product. This avermectin compound of the formula (I) is known to be of value as antiparasitic agents. This process results in a significant improvement in the overall yield.

BACKGROUND ART

In accordance with the prior art, there has already been described certain compounds which are known to be of value as antiparasitic agents. Included among these are such avermectin compounds which are described and claimed by Bishop Bernard Frank et al., in International Publication Number WO 94/15944, and by Fisher, Michael H. et. al., in European Publication Number EP 0 379 341 A2. However, according to the above conventional methods, the yield of the final reaction product was not always satisfactory. It is an object of this invention to convert the avermectin compound of formula (II) to avermectin compound of the formula (I) in high yield.

BRIEF DESCRIPTION OF THE INVENTION

The present invention provides a process for preparing a compound of the formula

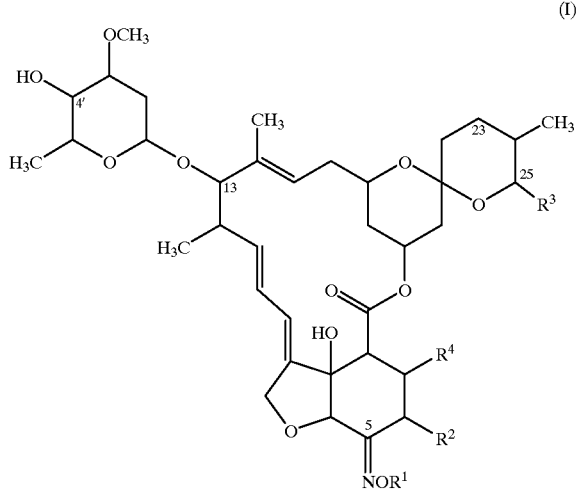

(I)

wherein $R^1$ is H or a hydroxyimino-protecting group; $R^2$ is H, $C_{1-4}$ alkyl or $C_{1-4}$ alkoxy; $R^3$ is $C_{1-8}$ alkyl (preferably $C_{1-4}$ alkyl), $C_{2-8}$ alkenyl (preferably $C_{2-5}$ alkenyl) or $C_{3-8}$ cycloalkyl (preferably cyclohexyl); and $R^4$ is H, halo, $C_{1-4}$ alkyl or $C_{1-4}$ alkoxy, which process comprises the steps of:

(a) reacting a compound of formula (II):

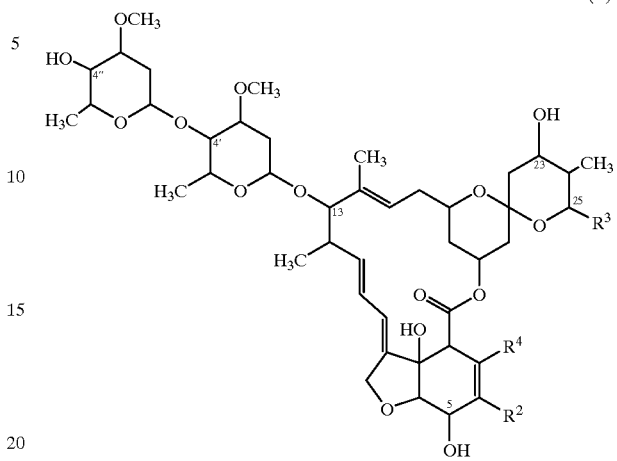

(II)

with an oxidizing agent to form a 5-oxo compound;

(b) allowing the 5-oxo compound to react with a compound of formula $R^1$—O—$NH_2$ wherein $R^1$ is H or a hydroxyimino-protecting group, to form a 5-imino compound;

(c) reacting the 5-imino compound with a thionocarbonizing agent to form a 4", 23-bisthionocarbonyl ester;

(d) reacting the 4", 23-bisthionocarbonyl ester with a deoxygenation agent to form a 4",23-dideoxy compound; and (e) reacting the 4", 23-dideoxy compound with an acid to form a compound of the formula (I).

This process further comprises, when $R^1$ is H, adding halotriphenylsilane, tert-butyldimethylsilane, halotrimethylsilane, halo(halomethyl)silane, haloallyldimethylsilane, halotriethylsilane, halotriisopropylsilane, halo(3-cyanopropyl)dimethylsilane, halodimethylloctylsilane, halotribenzylsilane, halotrihexylsilane or the like (preferably halotriphenylsilane), and triethylamine, tri-n-propylamine, diisopropylethylamine, imidazole, pyridine or 4-dimethylaminopyridine after the step (b) to protect the hydroxyimino group. Also, the reaction in step (e) (optionally followed by deprotection process) may be carried out in the presence of a palladium catalyst when $R^1$ is an allyl group. As previously indicated, the final products produced by this process of the present invention are useful compounds as antiparasitic agents.

DETAILED DESCRIPTION OF THE INVENTION

As used herein, the term "$C_{1-8}$ alkyl" means straight or branched chain saturated radicals of 1 to 8 carbon atoms, including, but not limited to methyl, ethyl, n-propyl, iso-propyl, n-butyl, iso-butyl, secondary-butyl, tertiary-butyl, pentyl, hexyl, and the like.

As used herein, the term "$C_{2-8}$ alkenyl" means straight or branched chain unsaturated radicals of 2 to 8 carbon atoms, including, but not limited to 1-ethenyl, 1-propenyl, 2-propenyl, 1-butenyl, 2-butenyl, 2-methyl-1-propenyl and the like.

As used herein, the term "$C_{3-8}$ cycloalkyl" means carbocyclic radicals, of 3 to 8 carbon atoms, including, but not limited to cyclopropyl, cyclobutyl, cyclopentyl, cyclohexyl, and the like.

As used herein, the term "halo" means fluoro, chloro, bromo or iodo.

As used herein, the term "allyl group" means alkyl or substituted alkyl group having a carbon-carbon double bond at the 2,3-position, including, but not limited to allyl, methylallyl, crotyl, chloroallyl, cinnamyl, and the like.

The process of the invention is described in detail herein below.

In the reaction in step (a), a compound of formula (II):

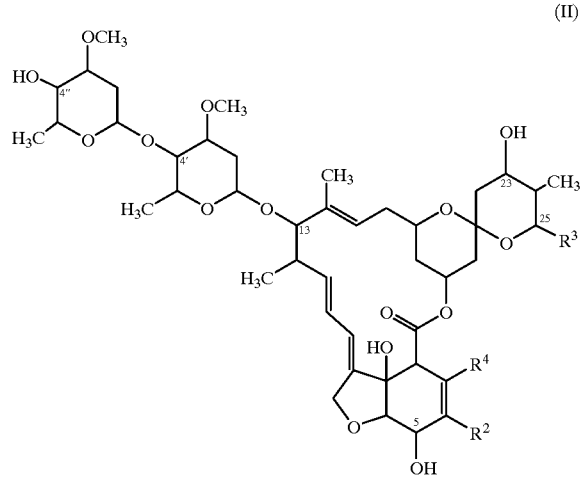

is reacted with an oxidizing agent to form a corresponding 5-oxo compound. More specifically, in this reaction, a hydroxyl group at the 5-position of the compound (II) is converted to an oxo group by oxidation. The compound of the formula (II) is an avermectin B2 compound which is a fermentation derived avermectin product. The compound of formula (II) can be isolated via fermentation of an avermectin producing strain of Streptomyces avermitilis such as ATCC 31267, 31271 or 31272, as described in U.S. Pat. No. 5,089,480. Other methods for obtaining the compound of formula (II) includes isolation from the fermentation broth of Streptomyces avermitilis ATCC 53568, as described in Dutton et al., Journal of Antibiotics, 44, 357–65 (1991).

Suitable oxidizing agents include, for example, manganese dioxide, nickel peroxide or pyridinium dichromate. Preferred is manganese dioxide in view of the selective oxidation of the α-position of a double bond. The oxidizing agent used in step (a) may be used in an amount of from 1 to 200 equivalents, preferably from 10 to 70 equivalents, against the compound of the formula (II) to be treated. The reaction in step (a) may be carried out at a temperature of 0 to 80° C. for 10 minutes to 10 hours. This reaction may be carried out in an inert solvent selected from, but no limited to chloroform, dichloromethane, benzene, toluene, xylene, tetrahydrofuran, dioxane, dimethylformamide, acetone, acetonitrile, tert-butyl methyl ester and a mixture thereof. Preferred is dichloromethane.

In the reaction in step (b), the 5-oxo compound obtained is reacted with a compound of formula $R^1$—O—$NH_2$ wherein $R^1$ is H or a hydroxyimino-protecting group to form a 5-imino compound. Suitable hydroxyimino-protecting groups include, for example, triphenylsilyl, tert-butyldimethylsilyl, tetrahydropyranyl, methylthiomethyl, allyl, methylallyl, crotyl, chloroallyl, cinnamyl or allyoxycarbonyl (preferably triphenylsilyl or allyl [$CH_2$=$CHCH_2$—]). The iminizing agent used in step (b) ($R^1$—O—$NH_2$) may be used in an amount of from 0.5 to 50 equivalents, preferably from 1 to 10 equivalents, against the 5-oxo compound to be treated. The reaction in step (b) is carried out at a temperature of −10 to 80° C. for 5 minutes to 20 hours. This reaction may be carried out in an inert solvents selected from, but no limited to chloroform, dichloromethane, benzene, toluene, xylene, tetrahydrofuran, dioxane, dimethylformamide, methanol, tert-butyl methyl ether, acetonitrile, isopropanol, water and a mixture thereof. Preferred is a mixture of methanol, dioxane and water.

In the reaction in step (c), the 5-imino compound is reacted with a thionocarbonizing agent to form a 4", 23-bisthionocarbonyl ester. Suitable thionocarbonizing agents include, for example, $R^5O$—C(S)-halo or $R^5S$—C(S)-halo (preferably the halo is chloro) wherein $R^5$ is $C_{1-4}$ alkyl, phenyl or naphthyl, the phenyl or naphthyl being optionally substituted with one or two substituents selected from $C_{1-4}$ alkyl, $C_{1-4}$ alkoxy, halo-substituted $C_{1-4}$ alkyl, halo-substituted $C_{1-4}$ alkoxy, nitro, hydroxy, amino and halo. Preferred is phenyl chlorothionoformate. The thionocarbonizing agent used in step (c) may be used in an amount of from 1 to 20 equivalents, preferably from 2 to 5 equivalents, against the 5-imino compound to be treated. The reaction is carried out at a temperature of 0 to 130° C. for 5 minutes to 10 hours in an inert solvents selected from, but not limited to chloroform, dichloromethane, benzene, toluene, xylene, tetrahydrofuran, dioxane, dimethylformamide, acetonitrile, ethyl acetate and a mixture thereof. Preferred is toluene.

In the reaction in step (d), the 4", 23-bisthionocarbonyl ester is reacted with a radical deoxygenation agent to form a 4", 23-dideoxy compound. Suitable deoxygenation agents include, for example, tributyltin hydride, tris(trimethylsilyl)silane, triethylsilane, tripropylsilane, phenylsilane, diphenylsilane, triphenylsilane, dialkylphosphite or hypophosphorous acid. Preferred is tris(trimethylsilyl)silane with a radical initiator. Suitable radical initiator includes azobisisobutyronitrile. The radical deoxygenation agent used in step (d) may be used in an amount of from 1 to 10 equivalents, preferably from 2 to 4 equivalents, against the 4", 23-bisthionocarbonyl ester to be treated. The reaction is carried out at a temperature of 0 to 140° C. for 5 minutes to 15 hours in an inert solvents selected from, but not limited to chloroform, dichloromethane, benzene, toluene, xylene, tetrahydrofuran, dioxane, dimethylformamide and a mixture thereof. Preferred is toluene.

In the reaction in step (e), the 4", 23-dideoxy compound is reacted with an acid to form a compound of the formula (I). Suitable acids include, for example, p-toluenesulfonic acid, benzenesulfonic acid, HF, HCl, $H_2SO_4$, $H_3PO_4$ and $HClO_4$. Preferred is p-toluenesulfonic acid. The acid used in step (e) may be used in an amount of from 0.01 to 20 equivalents, preferably from 0.5 to 5 equivalents, against the 4", 23-dideoxy compound to be treated. The reaction is carried out at a temperature of 0 to 100° C. for 5 minutes to 15 hours in an inert solvents selected from, but not limited to chloroform, dichloromethane, benzene, toluene, xylene, tetrahydrofuran, dioxane, dimethylformamide, methanol, ethanol, isopropanol, butanol, acetone, ethyl acetate, water and a mixture thereof. Preferred is methanol.

Also, in step (e), when, to deprotect the allyl group, the deprotection reaction is carried out in the presence of a palladium catalyst, the palladium catalyst is a palladium compound capable of easily forming a π-allyl complex when reacted with an allyl compound. More suitable palladium catalyst includes, for example, one having a ligand such as tetrakis(triphenylphosphine)palladium(0), dichlorobis(triphenylphosphine)palladium (II), dichlorobis(acetonitrile)palladium (II) and dichlorobis (triisopropoxyphosphine)palladium (II) or palladium (II) diacetate in conjunction with triphenylphosphine or triethyl phosphite (Refer to Jiro Tsuji, "Transition Metals in Organic Synthesis", Kagakudojin, 1991). In a conventional method using formic acid as a deprotecting agent, the reaction is carried out in boiling dioxane, (Yamada, T., et. al., Tetrahedron Lett. 27, 2368 (1986). However, in the process of the present invention, the deprotection proceeds at room temperature because of high reaction speed in the present reaction system.

The palladium complex catalyst may be utilized in an amount sufficient to catalyze the deprotection reaction, generally in an amount of from 0.1 to 50 mole percent, preferably from 1 to 10 mole percent, of the 4", 23-dideoxy compound to be treated in step (e).

The deprotection reaction is carried out in a suitable reaction-inert solvent. Suitable solvents include hydroxyl group-containing solvents such as alcohols, e.g., methanol, ethanol, and water; and non-hydroxyl solvents include, for example, haloalkyl compounds such as dichloromethane and chloroform; esters such as methyl acetate and ethyl acetate; ethers such as diethyl ether and tetrahydrofuran; nitriles such as acetonitrile and propionitrile; ketones such as acetone and methyl ethyl ketone; and aromatic hydrocarbons such as benzene and toluene; and a mixture thereof.

The deprotection reaction may be carried out under substantially neutral conditions. Thus, the process of the present invention is useful in the synthesis using starting materials and final compounds which are sensitive to acidic or basic conditions.

Conditions for the deprotection reaction may be determined depending upon the kind of compounds to be treated, deprotecting agents, catalysts, solvents used, etc. In general, the deprotection reaction may be carried out at a temperature of from −20° C. to 100° C., preferably from 10° C. to 40° C. for from 1 min. to 18 hours, preferably from 5 min. to 6 hours.

The compounds of the formula (I) are useful as antiparasitic agents, and thus can be used in the treatment of fleas and heartworms in dogs and cats, nematodes in cats, or the like.

The following representative examples are illustrative of the invention and are not intended as a restriction on the scope of the invention.

EXAMPLES

The present invention is illustrated by the following examples. However, it should be understood that the invention is not limited to the specific details of these examples. Negative FAB mass spectra (FABMS) were recorded on a JEOL JMS-700. Infrared ray absorption spectra (IR) were measured by a Shimadzu infrared spectrometer (FTIR-8200PC). $^1$H and $^{13}$C-NMR spectra were recorded at 270 MHz and 67.5 MHz, respectively, by a JEOL NMR spectrometer (JNM-LA270). Chemical shifts are expressed in parts per million ($\delta$) relative to tetramethylsilane for $^1$H-NMR and CHCl$_3$ ($\delta$) for $^{13}$C-NMR.

Example 1

1-A. 5-Oxo-25-cyclohexylavermectin B2

5-Oxo-25-cyclohexylavermectin B2 (2.00 g, 2.18 mmol) was dissolved in methylene chloride (20 ml) and activated manganese dioxide (8.0 g) was added. The mixture was stirred at room temperature for 30 minutes and filtered with supplementary filtering agent (3 g). The filter cake was washed with methylene chloride (20 ml). The methylene chloride solution was combined and concentrated in vacuo to yield quantitatively the titled compound as a resin-like yellow crystal (1.99 g). The NMR (nuclear magnetic resonance) spectra of the titled compound was consistent with the characteristic signals of 5-oxo-avermectin B1a and 5-oxo-avermectin B2a in J. Agric. Food. Chem., 29, 881 (1981).

$^1$H-NMR $\delta$ 6.60 (s, 1H, 3-H), 3.42 (s, 2×3H, 4"-OCH$_3$, 4"-OCH$_3$).

IR (KBr, cm$^{-1}$) 1720, 1680, 1455.

1-B. 5-(O-Triphenylsilyloxyimino)-25-cyclohexylavermectin B2

5-Oxo-25-cyclohexyl-avermectin B2 (1.92 g, 2.10 mmol) was dissolved in a mixture of methanol (9.6 ml) and dioxane (9.6 ml), and a aqueous solution (2.0 ml) of hydroxylamine hydrochloride (451 mg, 6.49 mm) was added. After 2.5 hours, an aqueous solution (2 ml) of hydroxylamine hydrochloride (500 mg) was added, followed by addition of an aqueous solution (3 ml) of hydroxylamine hydrochloride (1.0 g) after 3.5 hours. The mixture was stirred at room temperature for 5 hours and extracted with ethyl acetate after addition of water. The layer of the ethyl acetate was washed by aqueous saturated salt (NaCl) solution, dried over sodium sulfate and filtered. The filtrate was concentrated in vacuo, and the residue was dissolved in methylene chloride. A white solid deposited was filtered by adding hexane. After being dried in vacuo, 5-hydroxyimino-25-cyclohexylavermectin B2 was obtained (1.90 g, 97% yield).

This 5-hydroxyimino-25-cyclohexylavermectin B2 (1.00 g, 1.08 mmol) was dissolved in tetrahydrofuran (5.0 ml), and cooled to 3–5° C. Chlorotriphenylsilane (951 mg, 3.23 mmol) and triethylamine (0.60 ml, 4.30 mmol) were added. After the reaction solution was warmed to room temperature and being stirred for 30 minutes, it was extracted with ethyl acetate adding water. The filtrate was concentrated in vacuo, and the residue was purified by chromatography on silica gel (extension solution is hexane-ethyl acetate, 1:1–2:3) to yield the titled compound as a light white resin-like crystal (1.09 g, 85% yield).

$^1$H-NMR $\delta$ 7.75–7.60 (m, 6H, aromatic), 7.48–7.32 (m, 9H, aromatic), 3.44 (s, 2×3H, 4'-OCH$_3$, 4"-OCH$_3$).

Negative FABMS m/e 1187 (M)$^-$.

1-C. 4", 23-Bis(phenoxythionocarbonyl)-5-(O-triphenylsilyloxyimino)-25-cyclohexylavermectin B2

5-(O-Triphenylsilyloxyimino)-25-cyclohexylavermectin B2 (1.09 g, 0.918 mmol) was dissolved in toluene (11 ml), and pyridine (3.3 ml, 40.8 mmol) was added. The solution was heated to 80° C., and phenyl chlorothionoformate (0.635 ml, 4.59 mmol) was added dropwise. The reaction mixture was stirred at 80° C. for 50 minutes and cooled to 3–5° C. After adding aqueous 0.2 N hydrochloric acid (20 ml), the mixture was extracted with toluene (10 ml). The aqueous layer was extracted with toluene (10 ml). Toluene extraction was combined and washed with saturated sodium hydrogen carbonate solution (20 ml) and aqueous saturated salt (NaCl) solution (20 ml). After drying by sodium sulfate and filtration, the filtrate was concentrated in vacuo and the residue was purified by chromatography on silica gel (extension solution is hexane-ethyl acetate, 7:2) to yield the titled compound as a light white resin-like crystal (1.26 g, 94% yield).

$^1$H-NMR $\delta$ 7.70–7.61 (m, 6H, aromatic), 7.48–7.24 (m, 15H, aromatic), 7.15–7.07 (m, 4H, aromatic), 3.46 (s, 3H, —OCH$_3$), 3.43 (s, 3H, —OCH$_3$).

IR (KBr, cm$^{-1}$) 3480, 2931, 1716.

Negative FABMS m/e 1459 (M)$^-$, 1201 (M—Ph$_3$SiH)$^-$.

1-D. 4"-Deoxy-22,23-dihydro-5-(O-triphenylsilyloxyimino)-25-cyclohexylavermectin B1

4",23-Bis(phenoxythionocarbonyl)-5-(O-triphenylsilyloxyimino)-25-cyclohexylavermectin B2 (1.26 g, 0.862 mmol) was dissolved in toluene (12.6 ml). Then, tributyltin hydride (0.93 ml, 3.46 mmol) and azobisisobutyronitrile (142 mg, 0.865 mmol) were added. The solution was heated to 100° C. stirred for 55 minutes and concentrated in vacuo (3 ml). The residue thus obtained was purified by chromatography on silica gel (extension solution is hexane-ethyl acetate, 4:1–5:2) to yield the titled compound as a light white resin-like crystal (748 mg, 75% yield)

$^1$H-NMR δ 7.70–7.60 (m, 6H), 7.48–7.30 (m, 9H), 5.99–5.91 (m, 1H), 5.85–5.69 (m, 2H), 5.50–5.33 (m, 2H), 5.00 (d, J=8.8 Hz, 1H), 4.88 (s, 1H), 4.81–4.62 (m, 2H), 4.00–3.52 (m, 6H), 3.50–3.42 (m, 1H), 3.42 (s, 3H), 3.36 (s, 3H), 3.25 (t, J=8.8 Hz, 1H), 3.11–3.00 (m, 1H), 2.58–2.46 (m, 1H), 2.38–2.12 (m, 3H), 2.08–1.90 (m, 4H), 1.85–1.05 (m, 38H), 0.90–0.70 (m, 4H).

$^{13}$C-NMR δ 173.2, 157.8, 155.6, 138.6, 138.2, 135.8, 135.0, 133.3, 132.7, 130.0, 127.6, 125.3, 124.8, 121.2, 118.4, 99.2, 97.4, 94.9, 81.9, 80.2, 79.3, 78.9, 78.5, 72.9, 72.3, 68.7, 68.6, 67.3, 67.1, 64.4, 56.6, 55.2, 46.4, 41.1, 39.9, 39.1, 38.5, 36.9, 36.2, 35.6, 34.6, 34.1, 33.9, 31.2, 30.6, 28.0, 26.9, 26.5, 25.1, 24.7, 23.4, 21.3, 20.1, 18.3, 17.5, 17.4, 15.1

IR (KBr, cm$^{-1}$) 3481, 2929, 2854, 1716.

Negative FABMS m/e 1155 (M)$^-$, 896 (M—Ph$_3$SiH)$^-$.

1-E. 22,23-Dihydro-5-hydroxyimino-25-cyclohexylavermectin B1 monosaccharide

4"-Deoxy-22,23-dihydro-5-(O-triphenylsilyloxyimino)-25-cyclohexylavermectin B1 (748 mg, 0.647 mmol) was dissolved in methanol (22.5 ml), and p-toluenesulfonic acid (246 mg, 1.29 mmol) was added. After being stirred at room temperature for 60 minutes, triethylamine (0.2 ml) was added and concentrated in vacuo. The residue concentrated was purified by chromatography on silica gel (extension solution is hexane-ethyl acetate, 1:1) to yield the titled compound as a colorless resin-like crystal (290 mg, 58% yield). The NMR (nuclear magnetic resonance) spectra of the titled compound was consistent with the characteristic signals of 22,23-dihydro-5-hydroxyimino-25-cyclohexylavermectin B1 monosaccharide synthesized by a method disclosed in International Publication Number WO 94/15944.

$^1$H-NMR δ 8.10 (s, 1H, =N—OH), 3.47 (s, 3H, 4'-OCH$_3$), 3.18 (t, J=9.1 Hz, 1H, 4'-H).

IR (KBr, cm$^{-1}$) 3450, 2920, 1715.

Example 2

2-A. 5-(O-Allyloxyimino)-25-cyclohexylavermectin B2

5-Oxo-25-cyclohexylavermectin B2 (993 mg, 1.09 mmol) prepared in Example 1-A was dissolved in a mixture of methanol (7.0 ml) and dioxane (7.0 ml), then aqueous of O-allylhydroxylamine hydrochloride (597 mg, 5.44 mmol) was added. After stirred at room temperature for 17 hours, water (20 ml) was added, and extracted with ethyl acetate (100 ml). Phase of the ethyl acetate was washed by saturated aqueous salt (NaCl) solution, dried over magnesium sulfate and filtered. The filtrate was concentrated in vacuo to yield the titled compound as a light yellow resin-like crystal (992 mg, 94% yield).

$^1$H-NMR δ 6.10–5.70 (m, 5H), 5.45–5.20 (m, 4H), 5.04–4.95 (m, 1H), 4.80–4.65 (m, 4H), 4.60 (s, 1H), 3.95 (s, 1H), 3.90–3.37 (m, 17H), 3.25 (t, J=9.1 Hz, 1H), 3.15 (t, J=9.1 Hz, 1H), 2.60–2.20 (m, 6H), 2.03–1.40 (m, 22H), 1.34–1.15 (m, 12H), 0.96–0.80 (m, 4H).

IR (KBr, cm$^{-1}$) 3527, 2931, 1735, 1718.

Negative FABMS m/e 968 (M–H)$^-$.

2-B. 5-(O-Allyloxyimino)-4",23-bis(phenoxythionocarbonyl)-25-cyclohexylavermectin B2

5-(O-Allyloxyimino)-25-cyclohexylavermectin B2 (992 mg, 1.02 mmol) was dissolved in toluene (10.7 ml), and pyridine (3.7 ml, 45.7 mmol) was added. The solution was heated to 70° C., and phenyl chlorothionoformate (0.64 ml, 4.62 mmol) was added dropwise. After stirred at 80–85° C. for 90 minutes, the mixture was cooled to room temperature and black oil deposited was washed with toluene (10 ml). Toluene was combined and diluted by ethyl acetate (60 ml). The ethyl acetate solution was washed with water (20 ml), aqueous 1 N hydrochloric acid (10 ml) and aqueous saturated sodium hydrogen carbonate solution (10 ml). After drying by magnesium sulfate and filtration, the filtrate was concentrated in vacuo and the residue was purified by chromatography on silica gel (extension solution is hexane-ethyl acetate, 60:16) to yield the titled compound as a light red resin-like crystal (949 mg, 75% yield).

$^1$H-NMR δ 7.50–7.05 (m, 10H, aromatic), 4.62 (s, 1H, 6-H), 3.48 (s, 3H, —OCH$_3$), 3.43 (s, 3H, —OCH$_3$).

Negative FABMS m/e 1241 (M)$^-$.

2-C. 5-(O-Allyloxyimino)-4"-deoxy-22,23-dihydro-25-cyclohexylavermectin B1

5-(O-Allyloxyimino)-4",23-bis(phenoxythionocarbonyl)-25-cyclohexylavermectin B2 (949 mg, 0.764 mmol) was dissolved in toluene (25 ml). Then, tris(trimethylsilyl)silane (0.71 ml, 2.36 mmol) and azobisisobutyronitrile (125 mg, 0.761 mmol) were added. The solution was stirred at 80–100° C. for 50 minutes, then concentrated in vacuo. The residue thus obtained was purified by chromatography on silica gel (extension solution is hexane-ethyl acetate, 4:1) to yield the titled compound as a light yellow resin-like crystal (356 mg, 50% yield).

$^1$H-NMR δ 3.42 (s, 3H, 4'-OCH$_3$), 3.37 (s, 3H, 4'-OCH$_3$), all aromatic signals were disappeared. IR (KBr, cm$^{-1}$) 3481, 2929, 2854, 1716, 1450

$^{13}$C-NMR δ 173.3, 150.3, 138.3, 135.0, 134.0, 132.4, 124.8, 124.5, 121.3, 118.4, 117.7, 99.2, 97.5, 94.9, 81.9, 80.3, 79.4, 78.6, 78.5, 75.9, 73.2, 72.4, 68.7, 67.3, 67.1, 64.5, 56.6, 55.2, 46.4, 41.0, 39.9, 39.2, 38.6, 36.9, 36.3, 35.7, 34.6, 34.1, 31.2, 30.6, 28.1, 26.8, 26.6, 24.7, 21.4, 20.1, 18.3, 17.4, 15.2.

Negative FABMS m/e 937 (M)$^-$.

2-D. 5-(O-Allyloxyimino)-22,23-dihydro-25-cyclohexylavermectin B1 monosaccharide 5-(O-Allyloxyimino)-4"-deoxy-22,23-dihydro-25-cyclohexylavermectin B1 (356 mg, 0.379 mmol) was dissolved in methanol (12 ml), and p-toluenesulfonic acid (108 mg, 0.568 mmol) was added. After being stirred at room temperature for 90 minutes, saturated sodium hydrogen carbonate solution (12 ml) was added. Thus, a white solid deposited was filtered, washed by water, then purified by chromatography on silica gel (extension solution is hexane-ethyl acetate, 3:1) to yield the titled compound as a colorless resin-like crystal (218 mg, 73% yield)

$^1$H-NMR δ 6.10–5.90 (m, 2H), 5.82–5.68 (m, 2H), 5.50–5.40 (m, 1H), 5.35–5.18 (m, 2H), 4.98 (d, J=7.0 Hz, 1H), 4.82 (d, J=2.9 Hz, 1H), 4.80–4.62 (m, 4H), 4.60 (s, 1H), 4.00–3.80 (m, 4H), 3.72–3.50 (m, 3H), 3.47 (s, 3H, 4'-OCH3), 3.39 (t, J=2.2 Hz, 1H), 3.16 (t, J=9.2 Hz, 1H), 3.06 (d, J=8.1 Hz, 1H), 2.62–2.45 (m, 2H), 2.40–2.18 (m, 3H), 2.03–1.09 (m, 31H), 0.91–0.72 (m, 4H).

Negative FABMS m/e 809 (M)$^-$.

2-E. 22,23-Dihydro-5-hydroxyimino-25-cyclohexylavermectin B1 monosaccharide 5-(O-Allyloxyimino)-22,23-dihydro-25-cyclohexylavermectin B1 monosaccharide (218 mg, 0.269 mmol), tetrakis(triphenylphosphine)palladium (32 mg, 0.028 mmol) and benzenesulfinic acid (69 mg, 0.485 mmol) were added to chloroform (2.5 ml). After the reaction mixture was stirred at room temperature for 1.5 hours, triphenylphosphine (72 mg, 0.274 mmol) was added, then tetrakis(triphenylphosphine)palladium (52 mg, 0.045 mmol) was added after 2 hours. After being stirred for 5.5 hours, the reaction solution was purified by chromatography on silica gel (extension solution is hexane-ethyl acetate, 2:1–1:1) to yield the titled compound as a colorless resin-like crystal (175 mg, 85% yield). The NMR (nuclear magnetic resonance) spectra of the titled compound was consistent with the characteristic signals of 22,23-dihydro-5-hydroxyimino-25-cyclohexylavermectin B1 monosaccharide synthesized by a method disclosed in International Publication number WO 94/15944.

$^1$H-NMR δ 8.10 (s, 1H, =N—OH), 3.47 (s, 3H, 4'-OCH$_3$), 3.18 (t, J=9.1 Hz, 1H, 4'-H).

IR (KBr, cm$^{-1}$) 3450, 2920, 1715.

What is claimed is:

1. A process for preparing a compound of the formula (I):

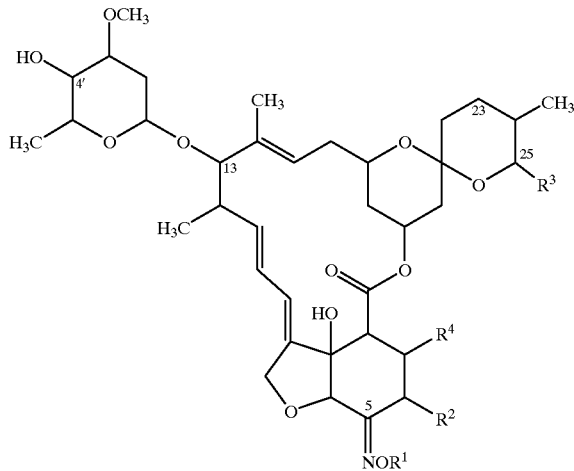

(I)

wherein R$^1$ is H or a hydroxyimino-protecting group; R$^2$ is H, C$_{1-4}$ alkyl or C$_{1-4}$ alkoxy; R$^3$ is C$_{1-8}$ alkyl, C$_{2-8}$ alkenyl or C$_{3-8}$ cycloalkyl; and R$^4$ is H, halo, C$_{1-4}$ alkyl or C$_{1-4}$ alkoxy, which process comprises the steps of:

(a) reacting a compound of formula (II):

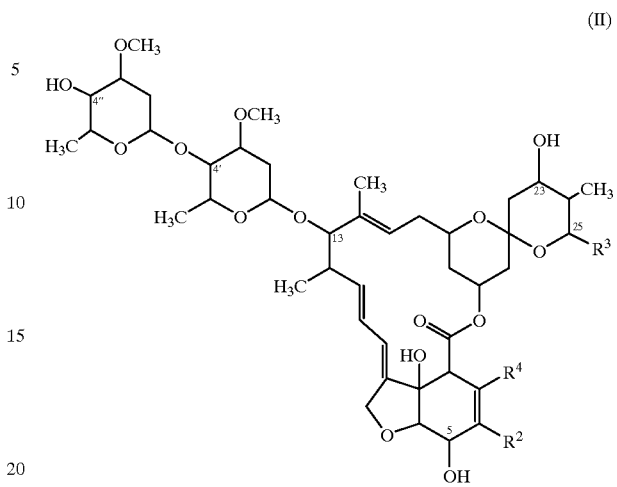

(II)

with an oxidizing agent to form a 5-oxo compound;

(b) allowing the 5-oxo compound to react with a compound of formula R$^1$—O—NH$_2$ wherein R$^1$ is H or a hydroxyimino-protecting group, to form a 5-imino compound;

(c) reacting the 5-imino compound with a thionocarbonizing agent to form a 4", 23-bisthionocarbonyl ester;

(d) reacting the 4", 23-bisthionocarbonyl ester with a deoxygenation agent to form a 4", 23-dideoxy compound; and (e) reacting the 4", 23-dideoxy compound with an acid to form a compound of the formula (I).

2. A process according to claim 1, which further comprises, when R$^1$ is H, adding halotriphenylsilane, tert-butyldimethylsilane, halotrimethylsilane, halo(halomethyl)silane, haloallyldimethylsilane, halotriethylsilane, halotriisopropylsilane, halo(3-cyanopropyl)dimethylsilane, halodimethylloctylsilane, halotribenzylsilane or halotrihexylsilane, and triethylamine, tri-n-propylamine, diisopropylethylamine, imidazole or pyridine after the step (b) to protect the hydroxyimino group.

3. A process according to claim 1, wherein the reaction in step (e) is carried out in the presence of a palladium catalyst when R$^1$ is an allyl group.

4. A process according to claim 1, wherein the oxidizing agent in step (a) is manganese dioxide, nickel peroxide or pyridinium dichromate.

5. A process according to claim 4 wherein the reaction in step (a) is carried out at a temperature of 0 to 80° C. for 10 minutes to 10 hours.

6. A process according to claim 1, wherein the hydroxyimino-protecting group in step (b) is triphenylsilyl, tert-butyldimethylsilyl, tetrahydropyranyl, methylthiomethyl, allyl, methylallyl, crotyl, chloroallyl, cinnamyl or allyloxycarbonyl.

7. A process according to claim 6, the reaction in step (b) is carried out at a temperature of 5 to 80° C. for 5 minutes to 20 hours.

8. A process according to claim 1, wherein the thionocarbonizing agent in step (c) is R$^5$O—C(S)-halo or R$^5$S—C(S)-halo wherein R$^5$ is C$_{1-4}$ alkyl, phenyl or naphthyl, the phenyl or naphthyl being optionally substituted with one or two substituents selected from the group consisting of $C_{1-4}$ alkyl, $C_{1-4}$ alkoxy, halo-substituted $C_{1-4}$ alkyl, halo-substituted $C_{1-4}$ alkoxy, nitro, hydroxy, amino and halo.

9. A process according to claim 8, the reaction in step (c) is carried out at a temperature of 0 to 130° C. for 5 minutes to 10 hours.

10. A process according to claim 1, wherein the radical deoxygenation agent in step (d) is tributyltin hydride, tris(trimethylsilyl)silane, triethylsilane, tripropylsilane, phenylsilane, diphenylsilane, triphenylsilane, dialkylphosphite or hypophosphorous acid.

11. A process according to claim 10, the reaction in step (d) is carried out at a temperature of 0 to 140° C. for 5 minutes to 15 hours.

12. A process according to claim 1, wherein the acid in step (e) is p-toluenesulfonic acid, benzenesulfonic acid, HF, HCl, $H_2SO_4$, $H_3PO_4$ or $HClO_4$.

13. A process according to claim 12, the reaction in step (e) is carried out at a temperature of 0 to 100° C. for 5 minutes to 15 hours.

14. A process according to claim 3, wherein the palladium catalyst is tetrakis(triphenylphosphine)palladium (0), dichlorobis(triphenylphosphine)palladium (II), dichlorobis(acetonitrile)palladium (II), dichlorobis(triisopropoxyphosphine)palladium (II) or palladium (II) diacetate.

* * * * *